(12) United States Patent
Muradian et al.

(10) Patent No.: US 6,780,656 B2
(45) Date of Patent: *Aug. 24, 2004

(54) CORRECTION OF OVERLAY OFFSET BETWEEN INSPECTION LAYERS

(75) Inventors: David Muradian, Yerevan (AM); John Caywood, Sunnyvale, CA (US); Brian Duffy, San Jose, CA (US); Julie Segal, Palo Alto, CA (US)

(73) Assignee: HPL Technologies, Inc., San Jose, CA (US)

( * ) Notice: Subject to any disclaimer, the term of this patent is extended or adjusted under 35 U.S.C. 154(b) by 249 days.

This patent is subject to a terminal disclaimer.

(21) Appl. No.: 09/972,742

(22) Filed: Oct. 5, 2001

(65) Prior Publication Data

US 2003/0160627 A1 Aug. 28, 2003

Related U.S. Application Data

(63) Continuation-in-part of application No. 09/747,497, filed on Dec. 22, 2000.
(60) Provisional application No. 60/233,343, filed on Sep. 18, 2000.

(51) Int. Cl.$^7$ .......................... H01L 21/66; G06F 19/00
(52) U.S. Cl. ......................................... 438/14; 702/83
(58) Field of Search .......................... 438/5, 7, 14, 16, 438/401; 702/81, 83–84; 700/121

(56) References Cited

U.S. PATENT DOCUMENTS

| | | | |
|---|---|---|---|
| 5,267,017 A | 11/1993 | Uritsky et al. | 356/375 |
| 5,539,752 A | 7/1996 | Berezin et al. | 371/221 |
| 5,777,901 A | 7/1998 | Berezin et al. | 364/578 |
| 5,870,187 A | 2/1999 | Uritsky et al. | 356/237 |
| 6,035,244 A | 3/2000 | Chen et al. | 700/110 |
| 6,586,263 B2 * | 7/2003 | Muradian et al. | 438/14 |

FOREIGN PATENT DOCUMENTS

EP 0 641 020 A2 A3 3/1995 ........... H01L/21/66

OTHER PUBLICATIONS

J. Segal et al, "Determining Redundancy Requirements for Memory Arrays with Critical Area Analysis", *Proceedings of the 1999 IEEE International Workshop on Memory Technology, Design, and Testing*, IEEE Comput. Soc., Aug. 1999.

J. Segal et al., "A Framework for Extracting Defect Density Information for Yield Modeling from In–line Defect Inspection for Real–time Prediction of Random Defect Limited Yields", *Proceedings of the 1999 IEEE International Symposium on Semiconductor Manufacturing*, (Piscataway, NJ: Institute of Electrical and Electronics Engineers), pp. 403–406. 1999 (no month).

J. Segal, et al, "Predicting Failing Bitmap Signatures for Memory Arrays with Critical Area Analysis", *1999 Proceedings IEEE/SEMI Advanced Semiconductor Manufacturing Conference and Workshop (ASMC)*, p. 178–182, 1999.

* cited by examiner

*Primary Examiner*—Evan Pert
(74) *Attorney, Agent, or Firm*—Sierra Patent Group, Ltd.

(57) ABSTRACT

A method for determining between at least three origins of a coordinate system used for at least three different defect inspection spaces. The method comprises: collecting multiple sets of data spanning defect inspection spaces; filtering the data sets to remove points that introduce noise into correlation calculations; determining whether different data sets show correlation; selecting pairs of data sets showing correlation greater than or equal to a metric; and calculating coordinate offsets of at least three origins based on the selected pairs of data sets.

18 Claims, 14 Drawing Sheets

- Prior Art -

CORRECTION OF OVERLAY OFFSET BETWEEN INSPECTION LAYERS

CLAIM OF PRIORITY

This application is a Continuation-in-Part application which claims the benefit of priority to U.S. patent application Ser. No. 09/747,497 filed Dec. 22, 2000, entitled "CORRECTION OF OVERLAY OFFSET BETWEEN INSPECTION LAYERS IN INTEGRATED CIRCUITS" which claims the benefit of priority to U.S. Provisional Application No. 60/233,343, filed Sep. 18, 2000, entitled "CORRECTION OF OVERLAY OFFSET BETWEEN INSPECTION LAYERS IN INTEGRATED CIRCUITS."

FIELD OF THE INVENTION

The present invention relates to the manufacturing of integrated circuits. More specifically, the present invention relates to identifying defects in integrated circuits being manufactured on a wafer.

PRIOR ART

Integrated circuits are commonly manufactured in batches on wafers. Multiple integrated circuits are manufactured on a single silicon wafer during the manufacturing process. Referring now to FIG. 1, there is shown a silicon wafer having a plurality of integrated circuits disposed thereon referenced by numbers 12, 14, 16, and 18.

During the manufacturing process, multiple masking processes are performed on the semiconductor wafer. Each masking process defines where features on various layers that make up the integrated circuit are to be positioned. For example, a layer of polycrystalline silicon may be deposited on a wafer. Then photosensitive resist is coated on the wafer and selectively exposed to light so that after developing the resist, the remaining resist forms a pattern. This pattern is then transferred to the polysilicon during an etch step so that after the remaining resist is removed, the polycrystalline silicon forms a pattern defined by the selective light exposure.

This masking and etching process sequence is repeatedly carried out on each wafer to create the intricate interconnected patterns of semiconductors, insulators, and metals needed to create the desired integrated circuit (IC).

The process described above is carried out to produce a plurality of IC's on a wafer as shown in FIG. 1. For example, a single silicon wafer may be the basis for tens to thousands of IC's. The ability to manufacture a plurality of IC's on a single silicon wafer reduces the overall cost of production, thereby passing these cost savings onto the consumer in the form of inexpensive IC's.

With advancements in technology, IC's have become very small and very complex. With each generation, IC features become smaller because of advancements in the manufacturing process described above. However, with these advancements it has become more difficult to detect defects.

As part of the manufacturing process, in an effort to reduce the number of defective IC dice, it is common to inspect all of, or a sample of, the dice on a sampling of the wafers being produced. The inspection may be an optical inspection with very sensitive optical instruments capable of detecting defects of the size of a minimum feature of the IC or might be an electrical test that, in the case of memories, is capable of locating the position of an electrical defect to within the area of one small cell. The artifacts that are detected serve to guide the engineers to where defects, which may lead to yield loss, occur.

Referring now to FIG. 1 there is shown a wafer having four dice labeled 12, 14, 16, and 18. The labeled dice illustrate how a wafer may be inspected during manufacturing. For example, each of these dice, either picked randomly or according to some reason, would be inspected for defects.

Referring now to FIG. 2, there is shown a hypothetical collection of defects that might be observed in an inspection report generated from inspecting the dice shown in FIG. 1. A line defect is illustrated on die 12 in FIG. 2. A line defect may be caused by a scratch on the wafer. Also shown on dice 12, 14, and 16 in FIG. 2, are a plurality of "point" defects 22, 26, 28, 34, 36, and 38. Also illustrated on die 11 in FIG. 2 is a large continuous defect 30 and a cluster of point defects 32.

Referring now to prior art FIG. 3, there are shown defects 42 through 68 that might be observed on another inspection report of the same dice later in the manufacturing process. The outline of the die is shown for illustrative purposes only in FIGS. 2 and 3 and would not be generally available in a standard defect inspection report.

Defects that occur on one layer may propagate through and also appear on subsequent levels during the manufacturing and inspection process. For example, a large contaminating particle that remains after cleaning of the polysilicon layer, might penetrate through the intervening dielectric layer and be seen on the metal contact layer. It is important to identify these propagating defects so that the cause of the defects can be correctly assigned.

After locating the defects, an overlay report may be generated in which the defects from the inspections of the successive layers are displayed together with the intention of identifying those defects that are reported to be at the same location on inspection of successive layers. However, experience has shown that there is an offset in the reported origin of the inspections between layers.

Referring now to FIG. 4, there is shown an exemplary overlay report as would be created after performing at least two inspections. As shown in FIG. 4, an offset in the origins of the coordinate systems used to report the location of the defects may cause the defects from one layer to-be incorrectly positioned with respect to those defects of a second layer. This offset has been a recurring problem in the manufacture of integrated circuits and, as the size of the integrated circuits features are reduced and the number of dice on a wafer increases, there is a growing need to correct this problem.

Thus, when an overlay inspection report is generated as shown in FIG. 4, propagating defects may not be identified. As shown in FIG. 4, only individual point defects from the defect clusters 32 and 62 would be selected. An attempt to identify correlated defects as those lying within some critical distance of each other would mistakenly select the pair of defects 48, both of which come from the second inspection. A more sophisticated correlation algorithm based on defects from successive inspections that lie within a critical distance would misidentify defects 45 and 26 as being correlated when in fact they are not.

Therefore, there is a need for a procedure for automatically detecting the origin offset between the inspections and correcting the offset in the overlay report so that the correlated defects that propagate between layers can be identified correctly. The present invention provides a method and apparatus for correcting these.

SUMMARY OF THE INVENTION

The present invention is directed towards a method for determining the offset between at least two origins of a coordinate system used for at least two different defect inspection spaces. The method comprises: collecting multiple sets of data spanning defect inspection spaces; filtering the data sets to remove points that introduce noise into correlation calculations; determining whether different data sets show correlation; selecting pairs of data sets showing correlation greater than or equal to a metric; and calculating coordinate offsets of the at least two origins based on the said selected pairs of said data sets.

The present invention is also directed towards a method for determining the offset between at least three origins of a coordinate system used for at least three different defect inspections of a wafer with integrated circuits disposed on it. An embodiment of the method comprises: finding all possible pairwise links between layers; constructing a tree of links; identifying all indirect paths along which layers can be linked; calculating statistics of offsets between indirectly linked layers; determining whether any pair of layers are linked by multiple paths; listing each pair of layers linked by multiple paths, if there are any pair of layers linked by multiple paths; selecting a listed pair of layers that have not been previously selected; determining whether offsets associated with said listed pair of layers are within confidence limits of each other; selecting the best estimate of said offsets; determining whether the system has selected all the of the listed pairs; and selecting a listed pair of layers that have not been previously selected.

The invention further relates to machine readable media on which are stored embodiments of the present invention. It is contemplated that any media suitable for retrieving instructions is within the scope of the present invention. By way of example, such media may take the form of magnetic, optical, or semiconductor media. The invention also relates to data structures that contain embodiments of the present invention, and to the transmission of data structures containing embodiments of the present invention.

DETAILED DESCRIPTION OF THE INVENTION

Those of ordinary skill in the art will realize that the following description of the present invention is illustrative only and not in any way limiting. Other embodiments of the invention will readily suggest themselves to such skilled persons.

In describing the present invention it is assumed that a wafer has been selected for which in-line inspection of data is available after the operations on two or more layers. In these descriptions, the problem of finding the offsets in the origins between the inspection data on two of the layers is described. From this disclosure it will be obvious that this operation can be readily and repeatedly applied on wafers having two or more layers. Additionally, the method of the present invention can be applied to wafers having more than two sets of inspection data.

Still further, the defect coordinates and the distance between the related defects are described in Cartesian coordinates. However, it will be obvious to one having ordinary skill in the art that the distance between related defects could be described in polar coordinates or may be described using other coordinate systems. The Cartesian coordinate system is typically used by the machines utilized to perform the inspection process. Therefore the present invention will be described in Cartesian coordinates as it will be the most convenient system to utilize.

Figure 7:
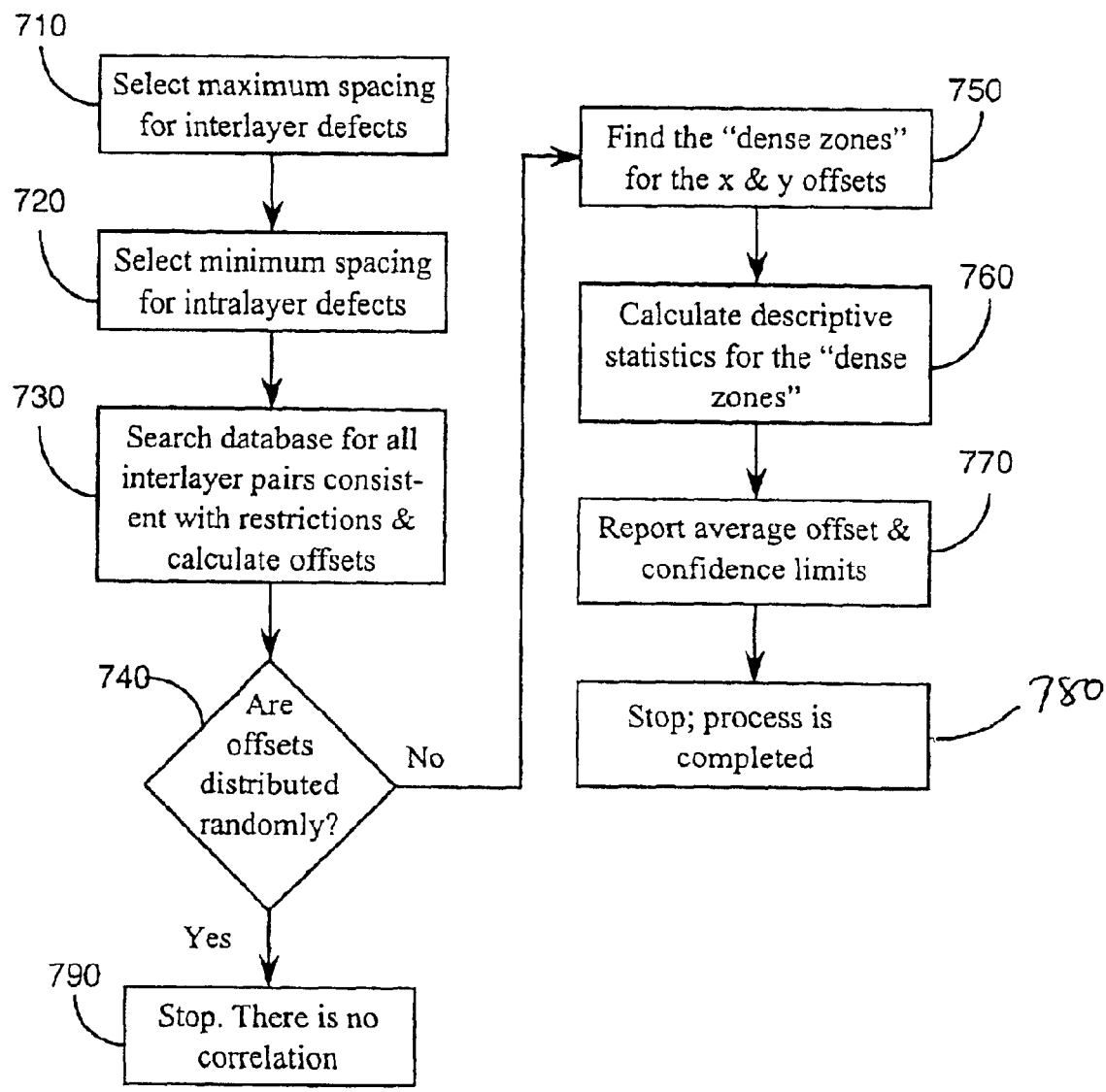
FIG. 7 is a function flow diagram illustrating the implementation of one method of the present invention.

Seven separate embodiments of the present invention are separately described herein. Referring now to FIG. 7, there is shown a functional flow diagram depicting a first method of the present invention.

At box 710, the method of the present invention begins with the setting of maximum X and Y values (Xmax and Ymax), e.g., the maximum allowed offsets between defects that propagate between layers during the manufacturing process. The values chosen by the user for Xmax and Ymax may vary depending upon the equipment utilized during the inspection process. The operator having knowledge of the equipment will chose appropriate values for Xmax and Ymax. For example, the operator may know from experience that the offsets are usually less than 60 micrometers.

At box 720, the minimum spacing allowed for intralayer defects Xint and Yint are established. The values for defects Xint and Yint are dependent upon the scale of technology being utilized in the manufacturing process. As an illustrative example, in the case of a technology with the minimum feature size of 0.5 micrometers, defects on the same inspection layer spaced closer than 10 micrometers might be considered to result from clustering.

In use, defects that are disposed closer together than the pre-set Xint and Yint values on the same inspection layer are excluded from the origin offset calculations. The minimum values may be selected by the user or they can be selected automatically by using the following formulas:

$Xint > 2*Xmax$ $Yint > 2*Ymax$

The limits for Xint and Yint are established to avoid confusion that may occur when there are two or more defects on one layer that can be overlaid on another defect that will be observed on a subsequent layer.

At box 730, a database is searched for all interlayer defect pairs consistent with the restrictions previously at box 710 and box 720. The process of box 730 may be performed after at least two inspections have been performed on the wafer. After locating all defect pairs that satisfy the restrictions previously selected (Xmax, Ymax, Xint, Yint), the offsets ΔX and ΔY in the coordinates of these defect pairs are calculated and saved for later use.

At Diamond 740 it is determined whether the offsets calculated in box 730 are distributed randomly with some selected probability. For example, the distribution could be tested to determine if the probability of the observed distribution occurring as a result of random processes is less than 1%. There are a number of methods known to those skilled in the art of performing statistical calculations that may be applied to achieve the desired results. See for example, Maurice G. Kendell and Alan Stuart, "The Advanced Theory of Statistics", Vol. 2 Inference and Relationship, Hafner Publishing Co., New York (1967).

If it is determined that the distribution could have occurred randomly, then the process proceeds to box 790 where the process stops. Alternatively, if it is determined that the distribution could not have occurred randomly, then the process proceeds to box 750.

Figure 5:
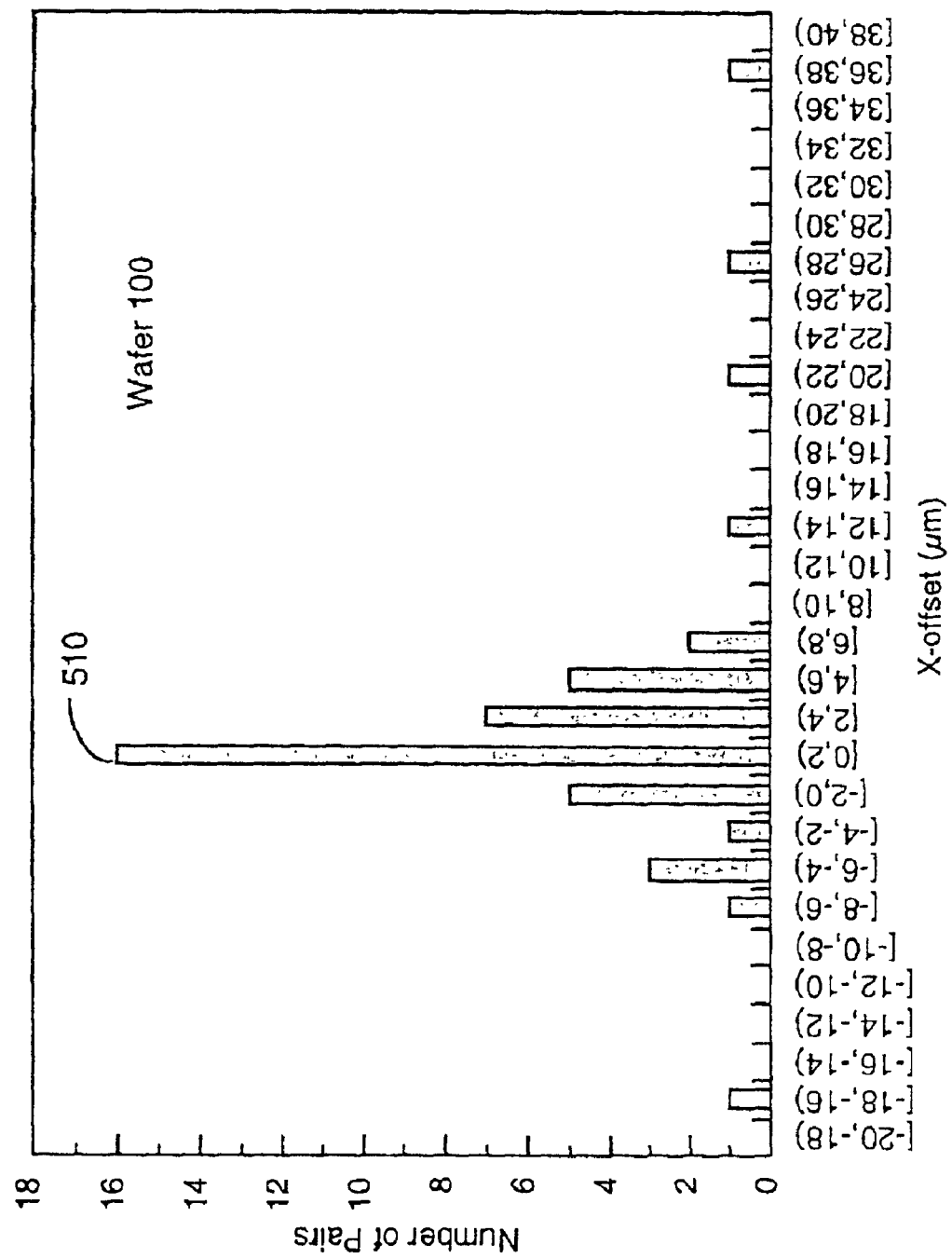
FIG. 5 is an illustration of the distributed offsets in the x-direction observed between defect pairs observed on two layers.
Figure 6:
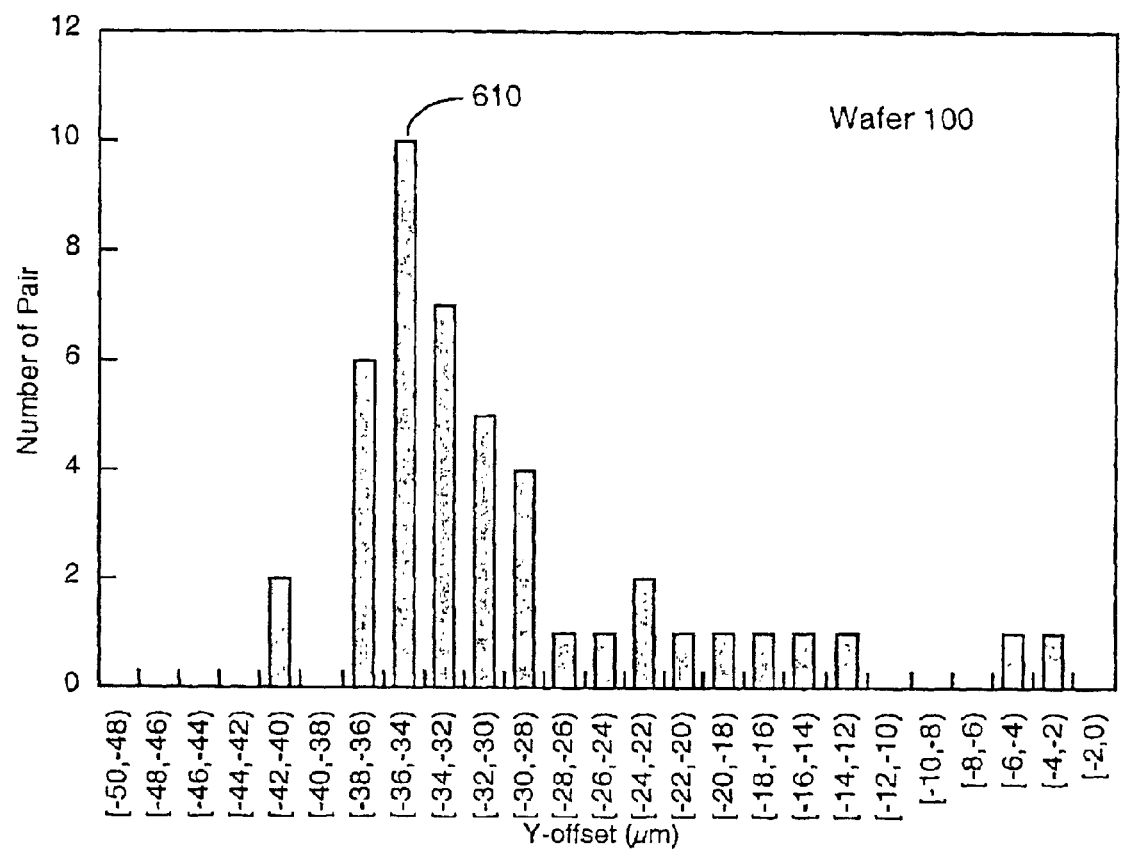
FIG. 6 is an illustration of the distributed offsets in the y-direction observed between defect pairs observed on two layers.

At box 750 the "dense zones" for the coordinate differences are determined as a result of the process of box 730. By "dense zones" is meant a region on each of the coordinate offset axes where there is a relatively high density of offsets found. In FIG. 5 it is seen that there is a relatively high density of offsets occurring in the range −8 μm to +8 μm. In FIG. 6 a similar cluster of offsets is observed between −42 μm and −28 μm.

The histograms of distances between pairs seen on a wafer for the x-coordinate and y-coordinate are shown in FIGS. 5 and 6, respectively. Referring now to FIG. 5, there is shown an exemplary histogram that may be generated during an inspection process undertaken on wafer 100. As shown in FIG. 5, there is a peak value 510 in the distribution of differences in the region between 0 and +2 μm.

Referring now to FIG. 6, there is shown an exemplary histogram that may be generated during an inspection process undertaken on wafer 100. As shown in FIG. 6, there is a peak value 610 in the distribution of differences in the region between −36 μm and −34 μm.

Each of the dense zones in FIGS. 5 and 6 have roughly a Gaussian distribution because the central limit theorem assures that the scatter in a number of observations that arise from several causes will tend to approximately a Gaussian distribution as the number of observations increases.

Referring now to FIG. 7, specifically box 750, there are a number of possible heuristic algorithms for determining the "dense zones." For example, the range of coordinate differences, Xmax and Ymax, could each be divided into a number of equal segments, e.g. 10 segments. The number of points falling into each segment are counted and the segments containing the greatest number of points falling within that segment for x-coordinate differences and for y-coordinate differences are selected as the most likely location of the dense zone.

Alternatively, the program can search for the set of intervals for which the count of observations is maximal using the following equations:

$$(\Delta Xupper - \Delta Xlower) < Xmax/10; \text{ and}$$

$$(\Delta Yupper - \Delta Ylower) < Ymax/10.$$

In the equations given above, ΔXupper is the upper value and ΔXlower is the lower value, respectively, for a segment of an ordered array of the ΔX values. ΔYupper and ΔYlower, are respectively the upper and lower values for a segment of an ordered array of ΔY values. The two examples described above are merely exemplary in nature and should not be considered limiting. As one who is skilled in the art will appreciate, there are many methods that may be utilized to determine the "dense zones"; each of which can be utilized with the invention described herein.

At box 760, after the dense zones have been identified, the standard descriptive statistics, i.e., the average, standard deviation, the upper and lower confidence limits, and an interval size for the confidence interval are calculated. The averages are taken as the best estimate of the offsets of the origins between the two layers and the confidence limits indicate the range within which the "true" offset is expected to lie. In this embodiment, the average is utilized as the estimate of the "true" offset both because of its intuitive appeal and because of its computational simplicity. It may be obvious to those ordinarily skilled in the art that other metrics could be utilized to define the "true" offset. For example, the median may be utilized as the estimate of the offset rather than the average. Similarly, one could use a maximum likelihood approach to estimate the "true" offset from the observations in the dense zones.

At box 770 the calculated offset and confidence limits are reported to the user so that they may be utilized to determine propagating dice and other defects on wafer 100.

At box 780, the process ends and is reset for use on the next wafer being processed.

Figure 8:
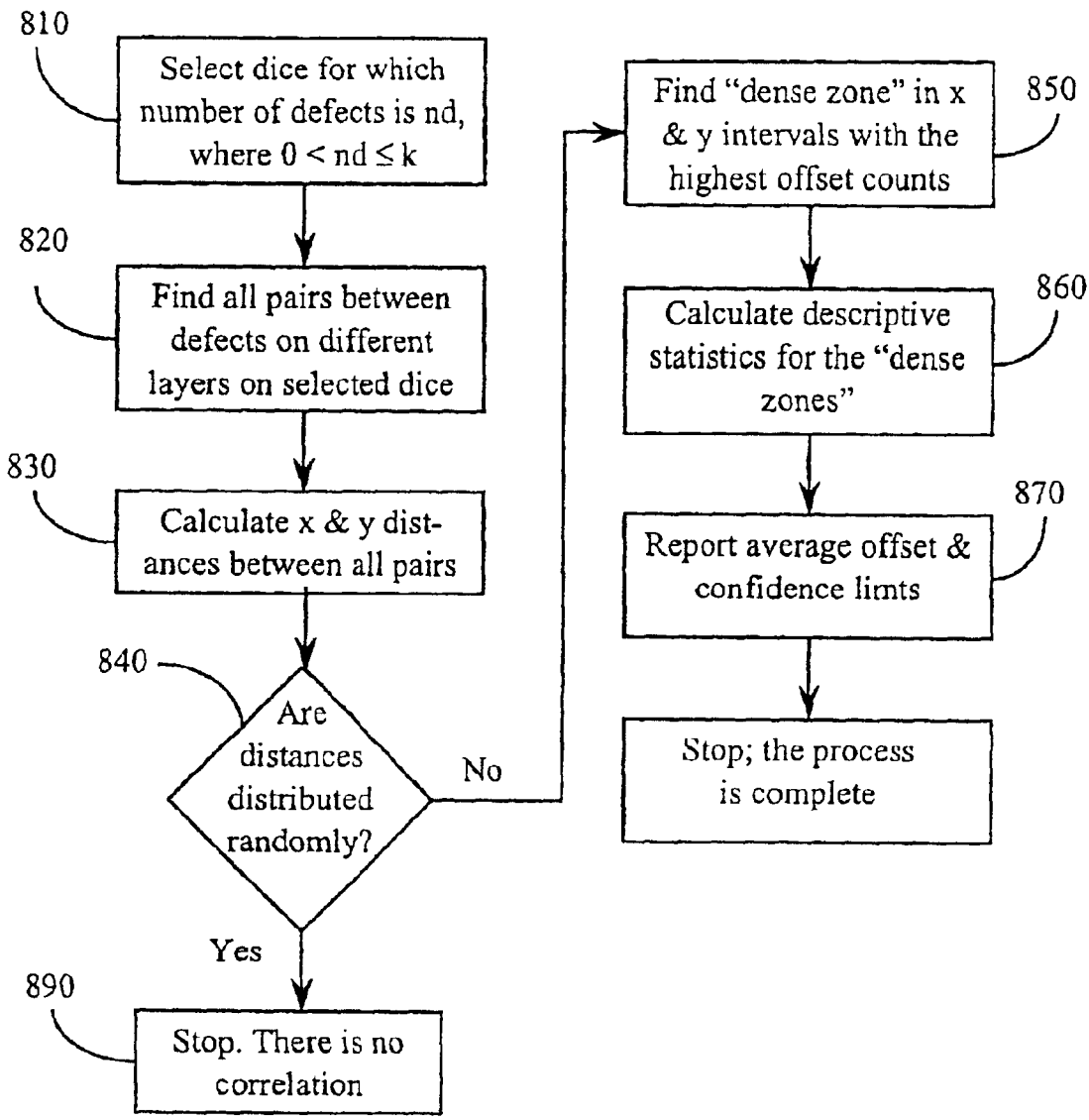
FIG. 8 is a functional flow diagram illustrating a second automated method of the present invention.

Referring now to FIG. 8, there is shown a functional flow diagram depicting a second automated method according to the present invention. With reference to FIG. 8, an automated process for determining offsets is described. The process is referred to herein as k-restricted sampling. The k-restricted sampling is applied to avoid the confusion that occurs when a defect is observed on one layer that can be overlaid on either two different defects on another layer. The k-restricted sampling of the present invention should not be confused with the k-statistics of R. A. Fisher.

Figure 1:
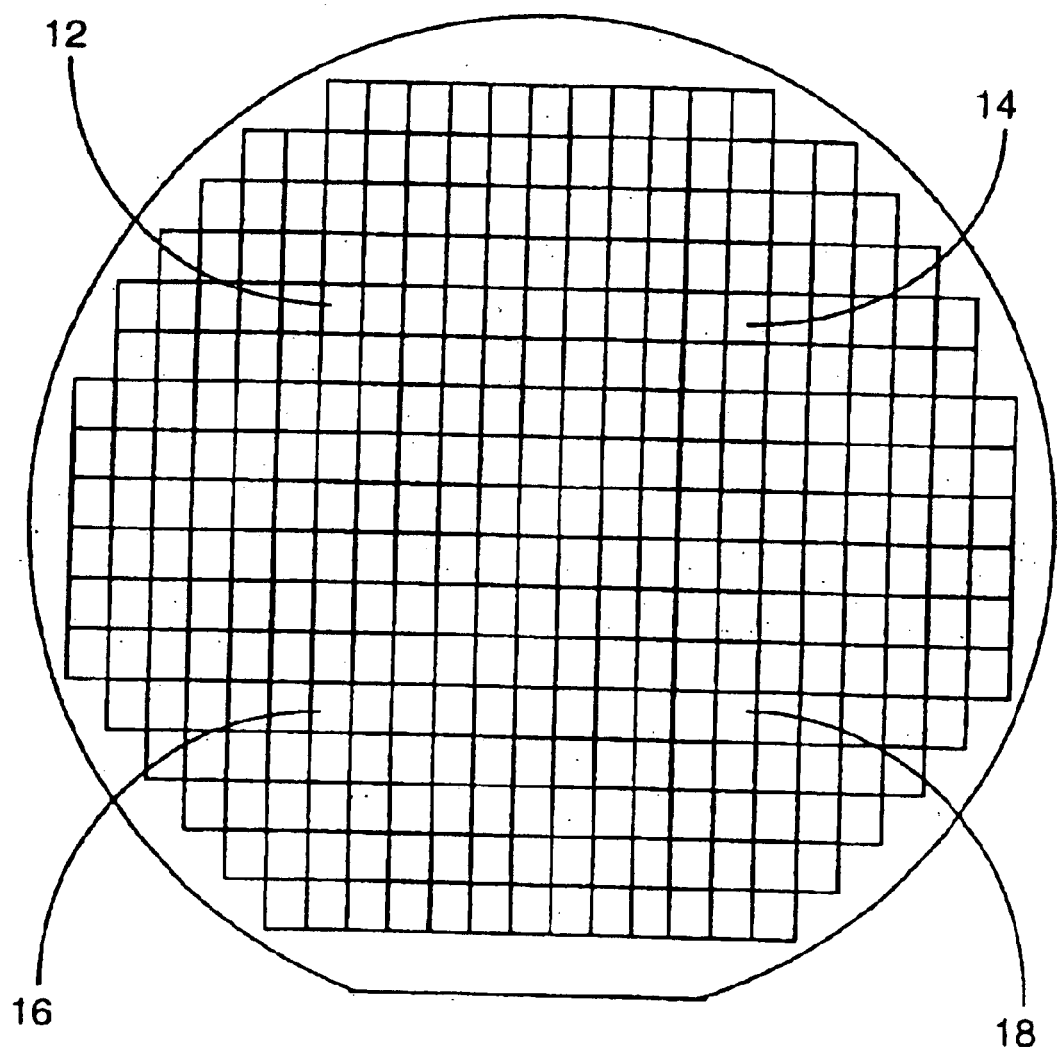
FIG. 1 is an illustration of a prior art wafer showing the division into an array of dice.
Figure 2:
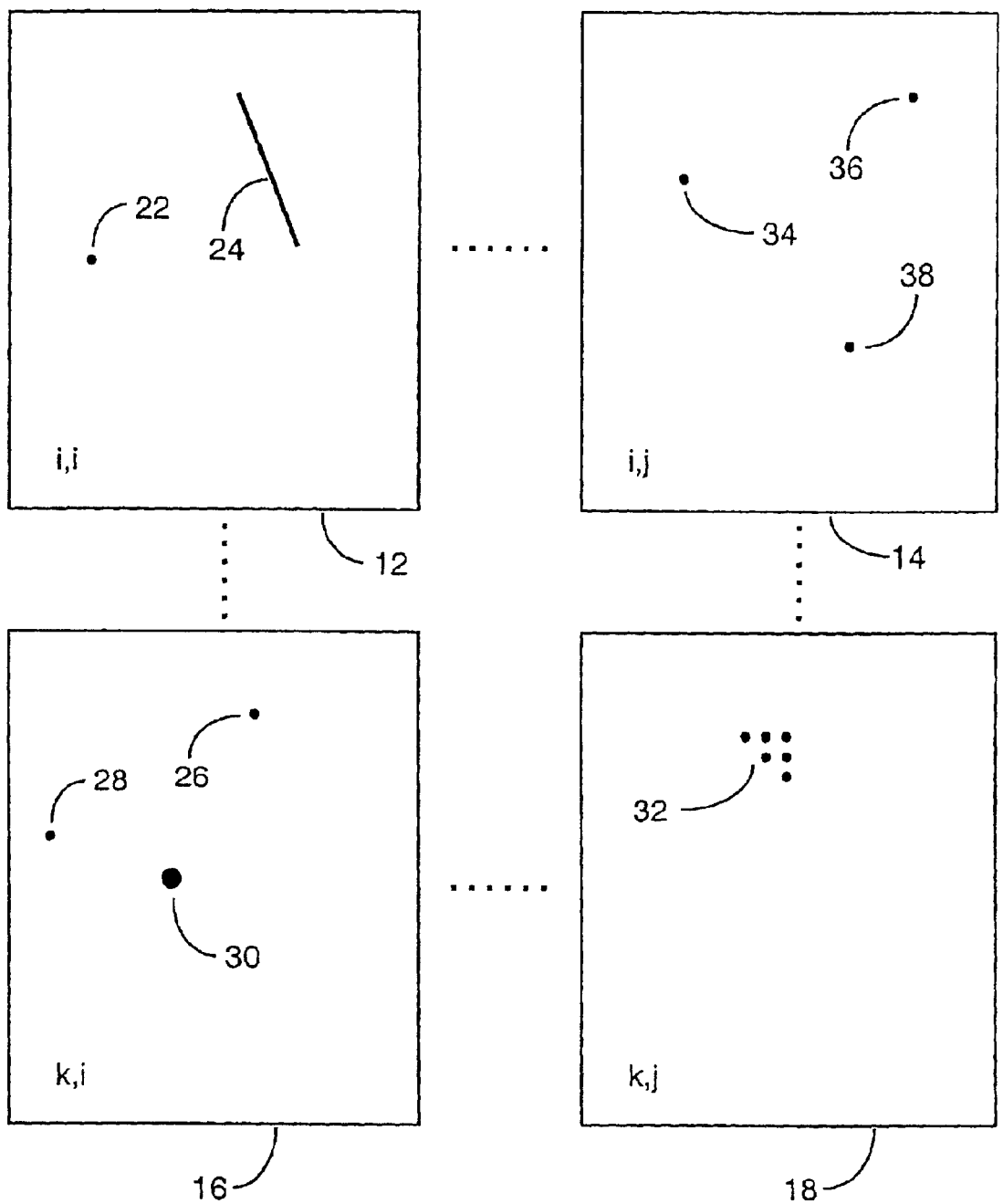
FIG. 2 is an exemplary illustration of defects that may be detected during an inspection process.
Figure 3:
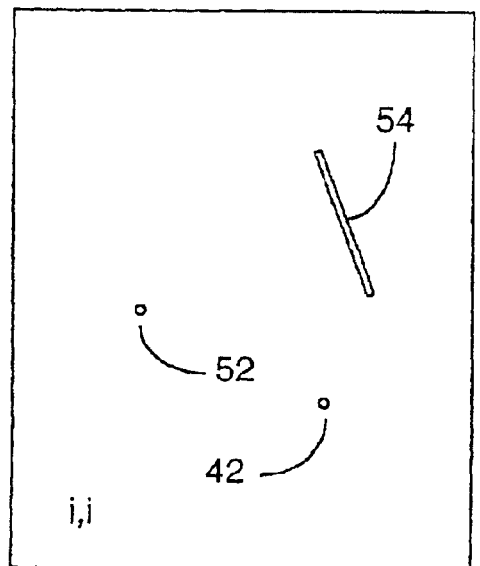
FIG. 3 is an illustration of defects that may be detected after a second layer has been processed on a wafer.
Figure 3:
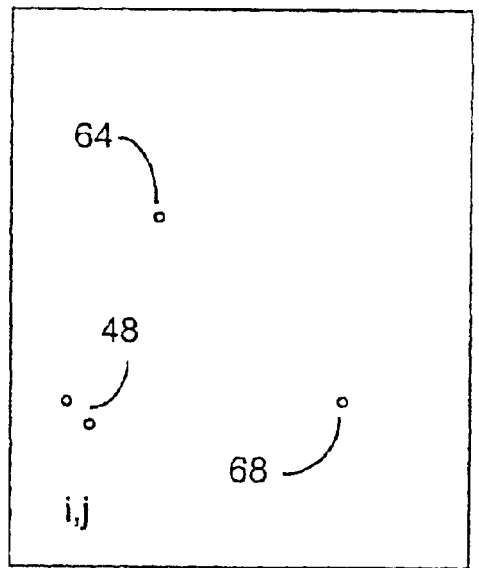
Figure 3:
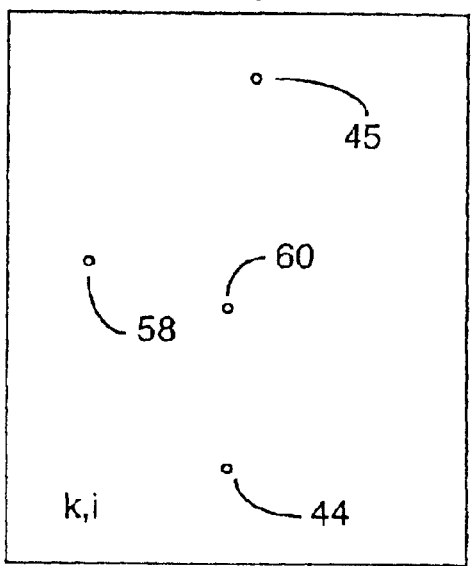
Figure 3:
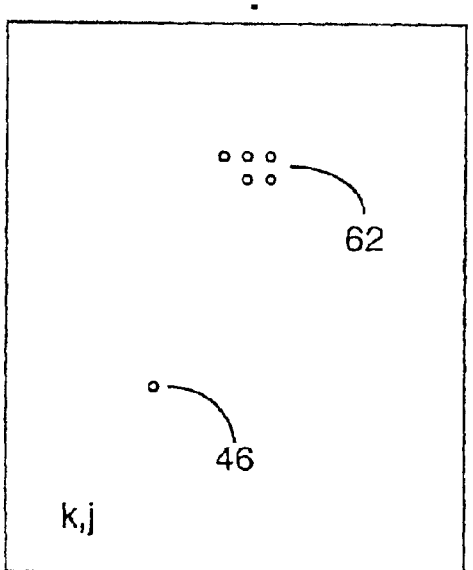
Figure 4:
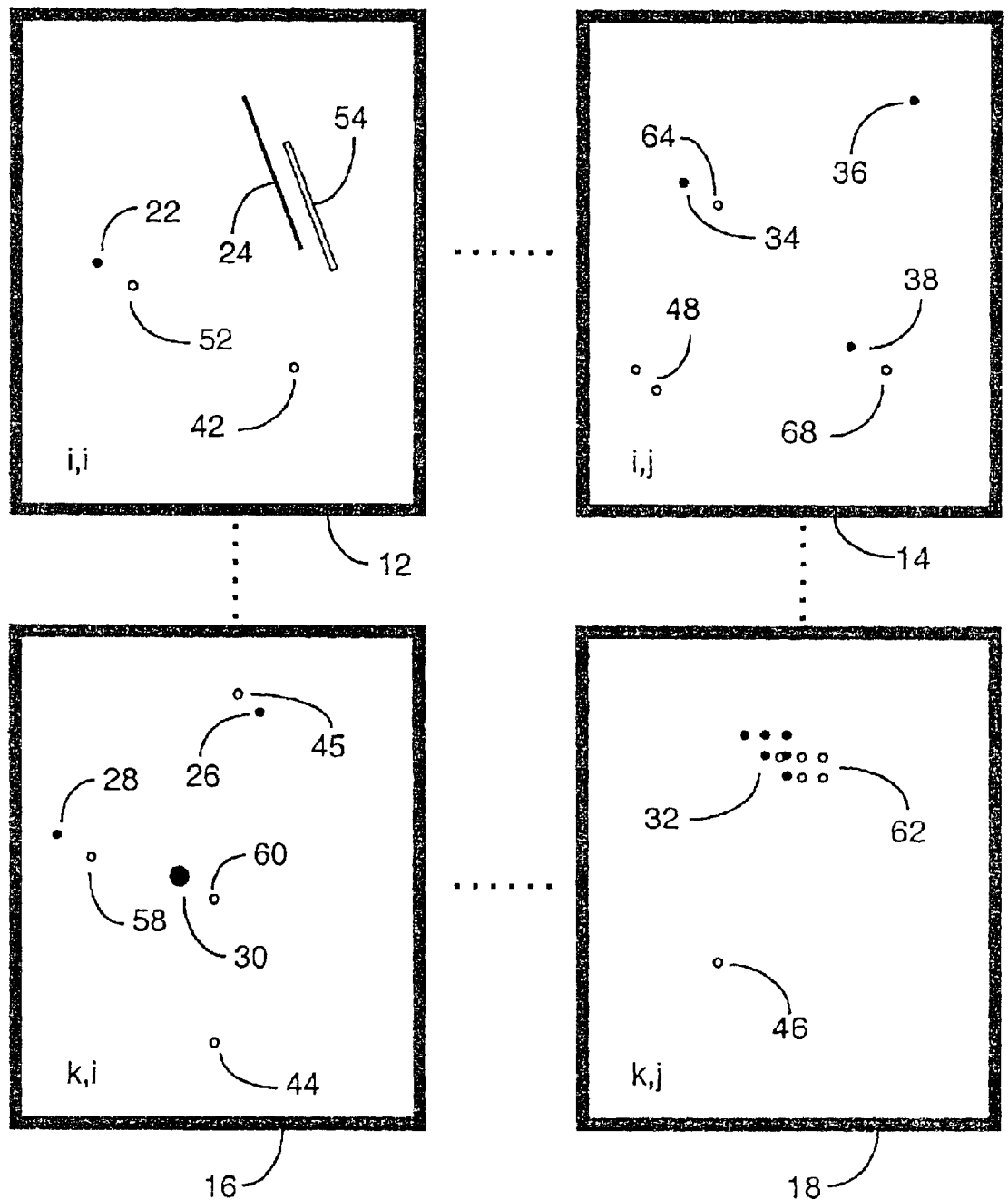
FIG. 4 is an illustration of an overlay report that may be created after at least two inspections showing defects as identified on different layers.

For example, the members of the cluster 32 and the members of the cluster 62 seen in FIG. 4 have the potential to confuse a calculation of offset. In the method described above, the restriction on the minimum spacing between defects on the same layer is used to remove clusters 32 and 62 from the offset calculation. In the embodiment disclosed with reference to FIG. 7, the restriction on the minimum spacing between defects on the same layer is used to remove the clustered defects 32 and 62 from the calculation. In an automatic embodiment of the present invention, the operator intervention of choosing Xmax and Ymax is eliminated.

Referring now to FIG. 8, at box 810, the values for Xmax and Ymax are taken to be the dimensions of the die under study. These values are extracted from the database. The problem of confusion of multiple defects is avoided by restricting the dice on which the calculations are carried out to those for which the number of defects, nd, satisfies the constraint $0 \leq nd \leq k$ where k is a small integer. Typically k is less than or equal to 3. If k is equal to 1, then the chance of confusion is zero. If, for example, k is set equal to 2, then assuming that for a die nd=2, and that none of the defects are propagating, 2 or 4 random pairs of ΔX and ΔY are introduced into the list of pair differences, depending upon whether there are two defects on both layers or on only one of the two layers. If one of the defects is propagating, there will be one matched pair and 1 or 3 random pairs introduced into the list of different pairs. If there are two propagating pairs, two matched pairs and no random pairs will be entered onto the list of different pairs.

This reasoning can be carried out on the k=n, but it becomes clear that the number of possibilities of random pairs increases faster than the possibilities of matched pairs so that the "noise" can overwhelm the "signal". For this reason, the value of k is chosen to be $\leq 3$, and is typically chosen to be 1 for a first try at determining the offset.

At box 820, all defect pairs are identified on selected dice on two different layers disposed on the wafer.

At box 830, $\Delta X$ and $\Delta Y$ of the pairs are determined according the process described above.

At Diamond 840, the newly determined $\Delta X$ and $\Delta Y$ pairs are tested to determine if they are distributed randomly. If the pairs are randomly distributed then the process advances to box 890 and the process stops. Alternatively, if it is determined that the pairs are not randomly distributed, there is an observed propagation of defects and the process advances to box 850.

At box 850, the dense zones for both X values and Y values are calculated as described above.

At box 860, after locating the dense zones, the process proceeds to calculate an estimate of the origin of the offset and its statistical uncertainty as described in the process above.

At box 870, the offset and the statistical uncertainty are displayed to the user.

At box 880, the process is ended and reset for use on the next wafer being processed.

When the automatic method described above and depicted in FIG. 8 is employed, the sample size of the number of pairs for which differences are calculated will be small in cases where there are few dice with a small number of defects. This may lead to more uncertainty in the estimate of the offset.

Each of the methods described herein may be utilized independently, or alternatively may be utilized concurrently. For example, the same data may be utilized for both processes. The user can then choose the calculated offset that gives the best result or utilize the result of the automatic approach as an input for the semi-automatic approach.

The problem of removing offsets between inspection data for different layers of a manufacturing process was discussed above. The example of layers given was the results of inspections performed after subsequent processing steps, e.g. inspections performed after, active area formation, poly definition and first layer metal definition.

However, layers may have the more general meaning of the results of separate inspections of an object. In integrated circuit manufacturing technology, separate layers could also mean multiple inspections of a wafer at the same point in the manufacturing flow performed with differing techniques, e.g. grazing angle laser scattering, dark field microscope inspection, and UV light induced fluorescence inspection. Layers could also mean the results of the repeated inspection of the same wafers at the same position is the manufacturing flow with the same tool as, for example is a test to determine the rate of particulate accumulation on a wafer. Similar examples could be found for other technologies.

Figure 9:
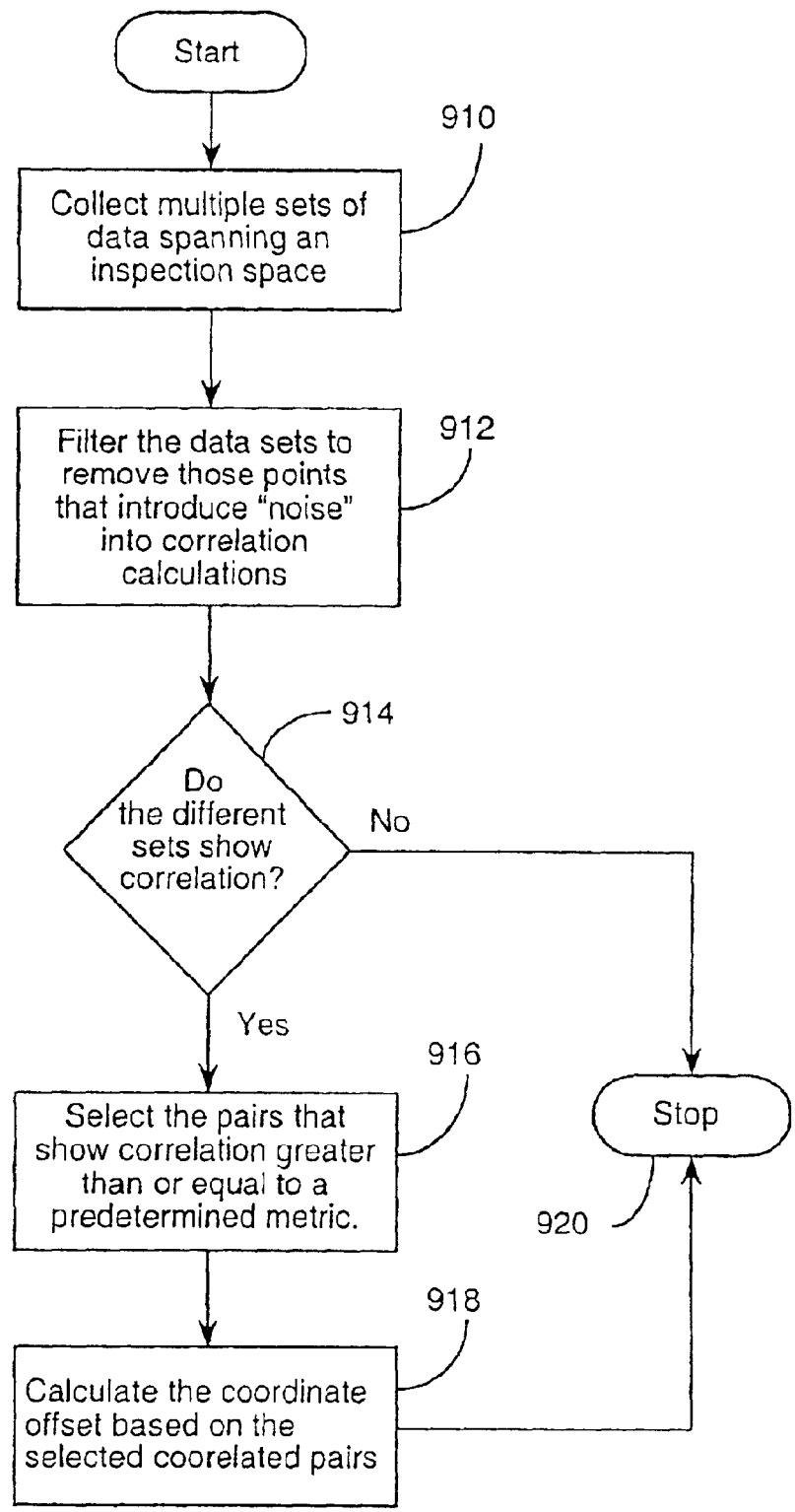
FIG. 9 is a flow diagram illustrating the implementation of one method of the present invention.

A generalized flow chart for the invention is shown in FIG. 9. FIGS. 7 and 8 are non-limiting examples of the general method, shown in FIG. 9, applied in a specific manner. First, more than one sets of inspection data are collected which cover an inspection space as indicated in act 910. In the examples given previously with regards to FIGS. 7 and 8, the inspection space is a planar surface, e.g. all or a portion of the surface of a wafer or a flat panel display. However, the method is clearly applicable to data sets from inspection of other forms as long as the location of points in the space can be described in an orthogonal coordinate system. The most obvious extension may be to curved two dimensional surfaces. For example, there is discussion of making displays that will fit on curved objects. It would still be possible to inspect the emitting surface of these displays and this inspection could be used to find the offsets between the origin of the coordinate systems used for multiple inspections. Further thought shows that the inspection spaces need not be limited to two-dimensional ones. For example, one could inspect the surface of a two-handled cup, which can not be mapped onto a simply connected two-dimensional surface, and use this invention to find the offsets between the coordinate systems for multiple inspections.

In general, it is useful to filter the data in one way or another in order to improve the "signal to noise level" between the features detected in one inspection which are correlated to features detected in another inspection as is shown in act 912.

An example of a filter is given in the implementation discussed previously in which features that were closer than a minimum distance on the same layer were discarded as were features on different levels that were located farther from each other than some maximum distance.

If the number of features is sufficiently sparse, filtering is not necessary, but the number of pairs available for calculating the offsets may be so low that the spread in the confidence limits associated with the result are fairly large. One way of dealing with this is to divide the inspection space into a number of spaces so that the number of features in each subspace is small enough that filtering within the subspace is not necessary. The spread in the confidence limits can be reduced in this approach by combining the results from the many subspaces. This is the approach used in the second embodiment of this invention with the addition of the filter that the number of features in a subspace must be less than some maximum. It should be clear from this discussion that an alternative approach would be to further subdivide any regions with an excessive number of features into two or more subregions such that the number in any one region meets the criterion that the number of features is sufficiently sparse.

After filtering, the sets are compared to see if the correlation between them exceeds some preset limit as indicated by the query 914. Means of testing for correlation are discussed in the following embodiments. Other means of testing for correlation are known to those of ordinary skill in the statistics art.

If the correlation does not exceed some preset minimum, stop the procedure. If the correlation does exceed this limit, the pairs showing correlation greater or equal to some predetermined metric are selected as is indicated in act 916. Means for such selection is discussed in other embodiments. Other means for this selection is known to those of ordinary skill in the statistics art.

As is indicated in act 918, the coordinate offsets are then calculated. Means for calculating these offsets and alternatives are discussed in the other embodiments herein.

Once the offsets are calculated, the procedure ends. The results may be reported to a user or employed in a procedure to, for example, automatically remove the offsets between the coordinates of the data sets so that the features observed in the inspection are stored and/or displayed "overlaid" on one another.

Figure 10:
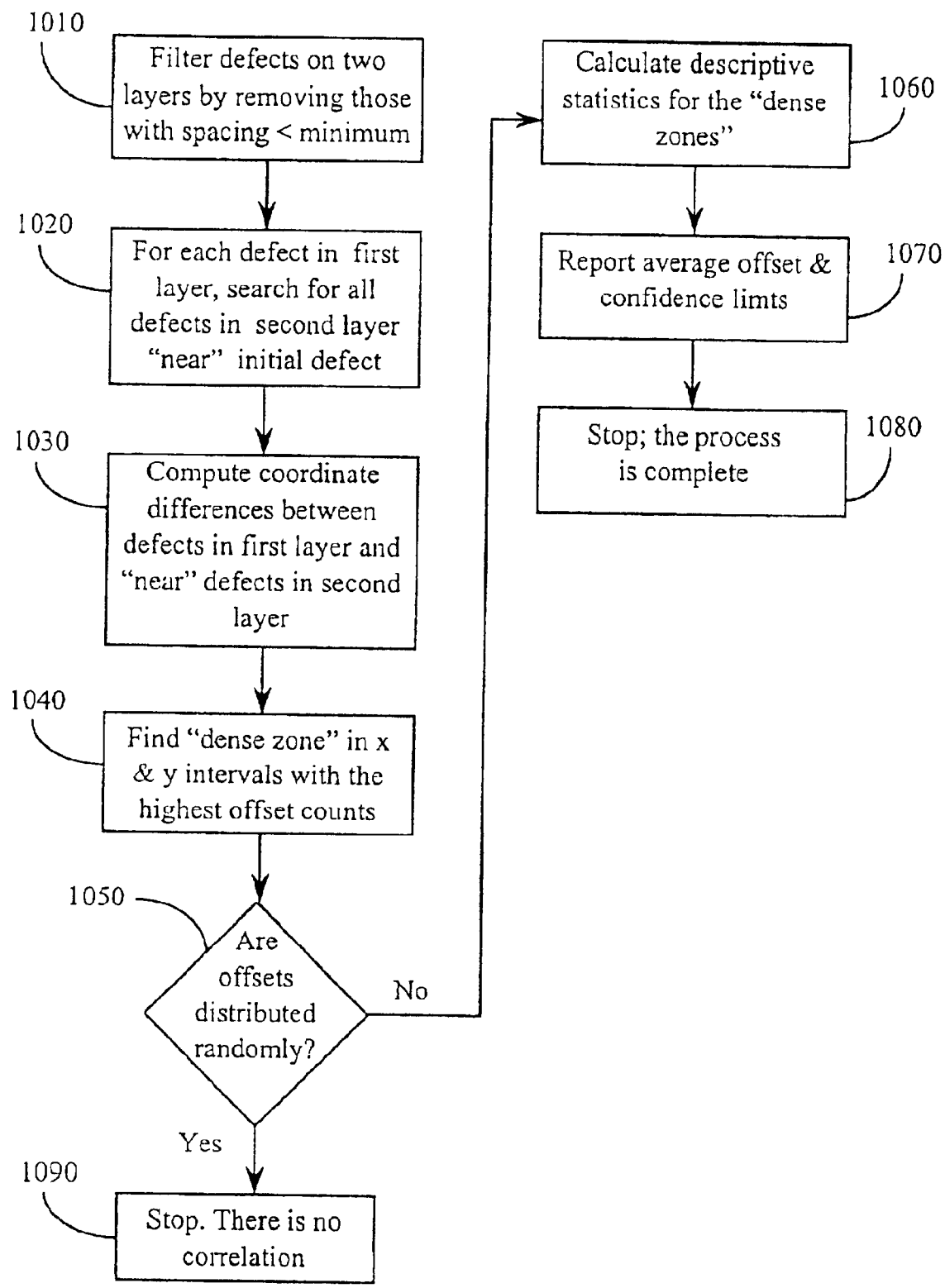
FIG. 10 is a flow diagram illustrating the implementation of one method of the present invention.

Another embodiment of an algorithm for finding the offset between the coordinate systems for two sets of inspection data from the same wafer is illustrated in the flow chart shown in FIG. 10. The method shown in FIG. 10 is also a non-limiting example of one embodiment of the more general method shown in FIG. 9, used in a specific application. The algorithm begins by filtering the data from each inspection and removing all defect clusters, i.e. all groups of defects for which the defects lie within some predetermined minimum data from each other as is indicated with the act 1010.

After filtering each inspection data set to remove clusters, one inspection set is defined as a first layer. This is normally the layer from which defects may propagate to the second layer. For each defect in the first layer, the region on the second layer within a rectangle of predetermined size centered on coordinate of the defect in the first layer is searched for defects as is indicated in act 1020. (It is often found convenient to choose the rectangle to be a square.) For each defect found, its offset from the center of the rectangle, $\Delta X$ and $\Delta Y$, is calculated as is indicated in act 1030.

The array of offsets, which extend from $-\Delta X_{max}$ to $+\Delta X_{max}$ in the x-coordinate and from $-\Delta Y_{max}$ to $+\Delta Y_{max}$ in the y-coordinate, is search for the rectangle of predetermined size $h_x \times h_y$) that contains the most points as is indicated in act 1040. This is defined as the "dense zone".

The dense zone will contain some p points. The question of whether the offsets are distributed randomly is determined by testing whether the probability that at least p of the offset pairs will lie within a rectangle of size ($h_x \times h_y$) is less than some predetermined small value, e.g. 0.05 as is indicated in query 1050. If it is, the distribution of offsets is not random. Other wise the offsets are taken to be a random distribution and the procedure stops as act 1090 shows.

If the distribution is not random, the descriptive statistics for the dense zone are calculated are calculated in act 1060 and reported in act 1070. After this, the algorithm terminates as is shown in 1080.

An electrical failure map is different is several ways from the defect maps generated from in-line inspection during processing. On the one hand, the electrical failures resulting from one localized defect can extend for long distances on a die. In the extreme case of a defect that causes a short between power supply traces at different potentials, e.g. $V_{DD}$ and ground, the entire die may fail. On the other hand, the electrical failure map is in some ways the principal layer because the usual goal of all of the inspections is to improve the die yield, i.e. to minimize the electrical failures.

In many practical cases such as bit failures in memory arrays, the location of the electrical defect may be restricted to a smaller area than the defects observed with the in-line inspections.

Finally, because the electrical test is performed after all of the layers used to form the integrated circuit are processed and, consequently, after all of the in-line inspections are performed, correlation may be possible between the electrical failure map and many or all of the in-line inspection maps. This is in contrast to the in-line inspection where a defect first observed at, for example, layer 3 will usually only propagate forward for a few layers and cannot propagate to layers previously inspected so that propagation is usually restricted to a few layers occurring near each other in the process sequence.

It is known that only a portion of the defects that are observed in with the in-line inspections will cause electrical failure either because of their location or their size. Those defects that cause electrical failures are often called "killer defects" and distinguished from "non-killer defects". However, in principle, the non-killer defects are no different than the defects that do not propagate from one layer to the next and are handled by the existing procedures.

Figure 11:
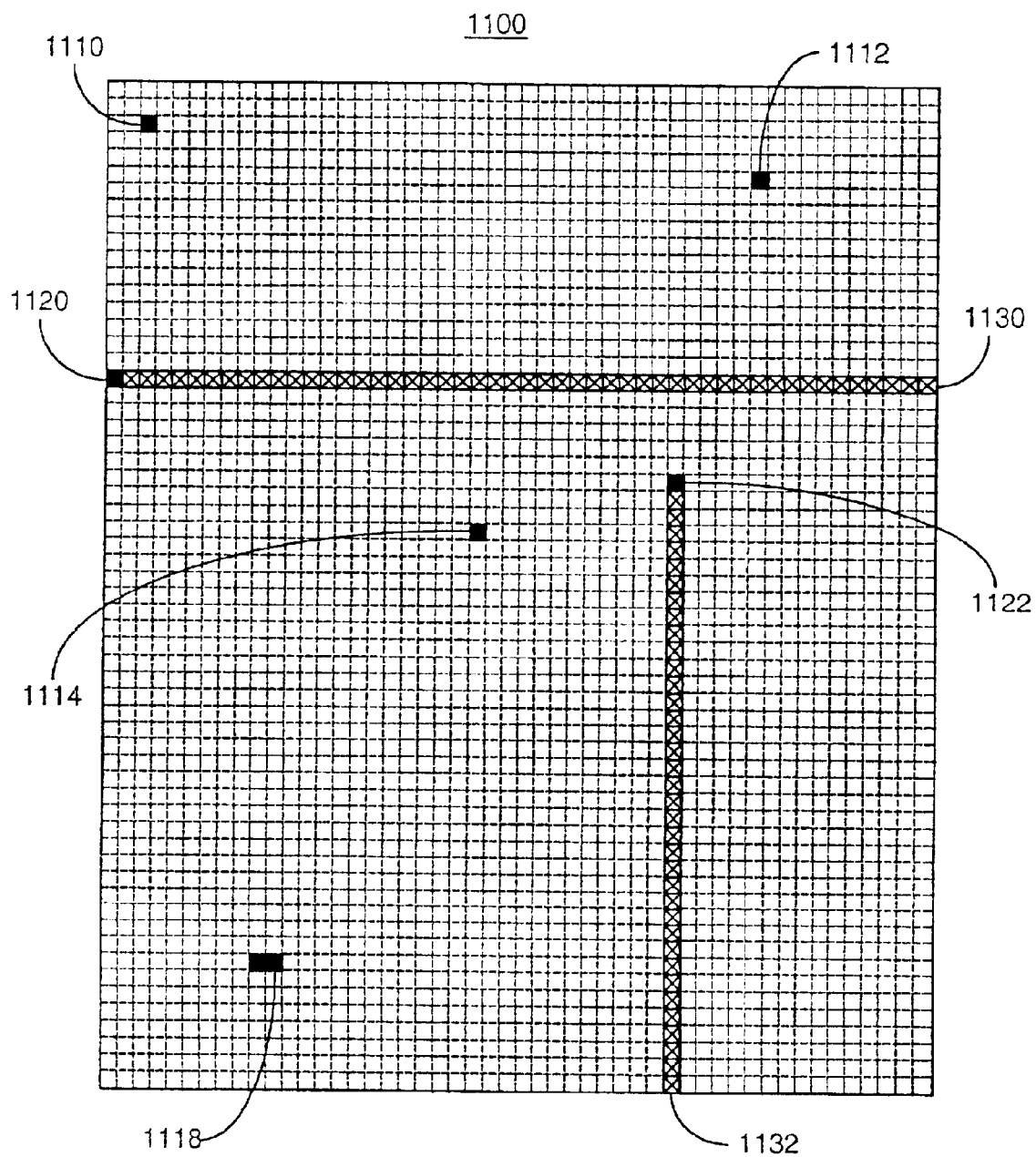
FIG. 11 is a schematic illustration of a portion of a memory array.

As was noted previously, local physical defects can cause extended electrical failures. The physical location of defects causing failures detected electrically is in general difficult to determine, however, in the special case of memory arrays this can often be determined with reasonable precision. FIG. 11 shows schematically a portion of a memory array, 1100. The memory cells are arrayed regularly along a number of rows and columns. The location of each cell is determined uniquely by specifying which row and column the cell lies on, i.e. the row and column addresses. In the cases that an isolated cell fails, such as is shown for cells 1110, 1112, and 1114, the defect can be assumed to lie within the area covered by the cell. In many modern memory technologies, the area occupied by a cell is <1 $\mu m^2$ so that the location is determined with some precision.

Unfortunately, not all failures involve only a single cell. Failures also appear as pairs of cells, shown as 1118, complete or partial rows, illustrated in 1130, complete or partial columns, illustrated as 1132, or other groups of cells. In the case of small, contiguous groups such as pairs, the defect can be assigned to the area covered by the cells included in the group. Other groups such as rows and columns, and clusters of closely spaced but discontinuous clumps of cells must be filtered out of the data before correlation studies are under taken as has been discussed for clusters of defects observed with in-line inspections.

In the very common special case in which a Cartesian coordinate system is employed, overlay information can be extracted from the row and column failures. Consider the row of bit failures in FIG. 11 labeled 1130. This row of failing bits could be the result of a short between the row select line, usually called the "word line", and ground in the cell location filled in and labeled 1120 in FIG. 11. However, a short between the word line and ground in one of the other cells along row 1130, indicated by crosses in FIG. 11 would also result in failure of all of the cell along the row. Therefore, the row failure gives no information as to the location of the underlying physical defect along the row, i.e. in the x direction. However, it is known the defect is located within a small range of y coordinates, i.e. the height of the row label 1130. Analogous arguments can be made with respect to the column labeled 1132.

Advantage can be taken of the additional information contained in the location of the row and column failures if the problem of finding the x and y coordinates of the offsets between electrical failures and defects observed with in-line inspection is separated into two independent problems, one for each coordinate, at the time of the filtering of the failures. In this approach the y locations of failing rows or partial rows are included in determination of the overlay offsets in the y direction and the locations of failing columns or partial columns are included in determination of the overlay offsets in the x direction.

After the overlay offsets have been determined between the various in-line inspections and between the defects observed with in-line inspection and the electrical failures, it is often observed that not all of the offsets are independent of each other.

Figure 12:
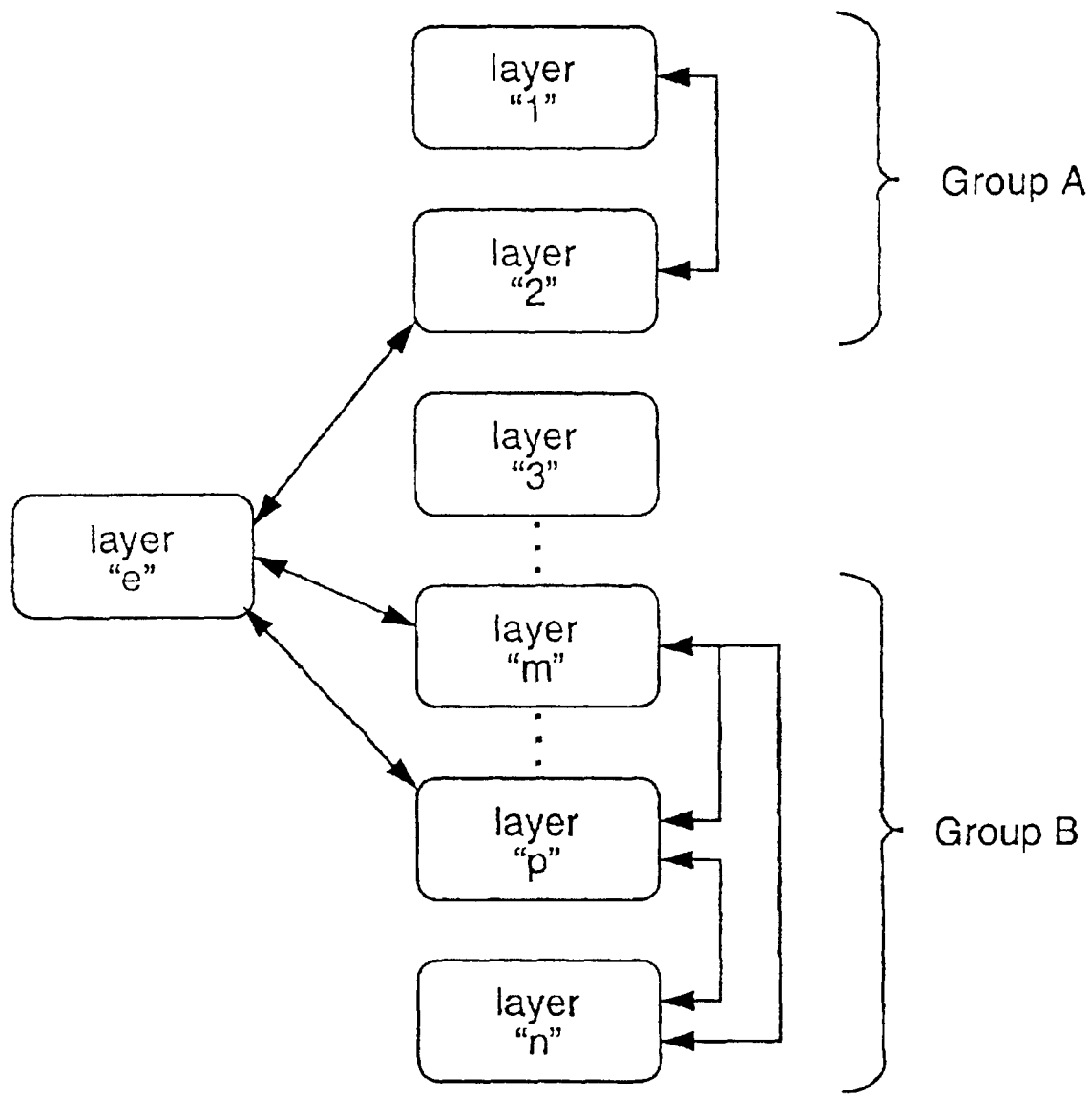
FIG. 12 is a schematic illustration of overlay offsets that have been obtained for various layers.

Consider FIG. 12. In this figure, the overlay offsets that have been obtained between the in-line inspections of the various process layers 1 through n and between the in-line inspections and the electrical failures, layer "e", are shown schematically. For example, the line with arrows between layers 1 and 2 indicate that an best estimate of the overlay offset (i.e. the average offset) has been determined between these layers so that it is known that:

$$x_1 = x_2 + \Delta X_{1,2} \text{ with some standard deviation } s(\Delta X_{1,2}) \quad \text{eq. 1a)}$$

and $$y_1 = y_2 + \Delta Y_{1,2} \text{ with some standard deviation } s(\Delta Y_{1,2}) \quad \text{eq. 1b)}$$

where the best offset estimate and its uncertainties have been determined from the defects lying in the dense zone, which number $N_{1,2}$. These offsets are determined by the equations:

$$\Delta X_{1,2} = \frac{\sum \Delta x_{1,2}}{N_{1,2}} \text{ and} \quad \text{eq. 2a)}$$

$$\Delta Y_{1,2} = \frac{\sum \Delta y_{1,2}}{N_{1,2}} \quad \text{eq. 2b)}$$

where $\Delta x_{1,2}$ and $\Delta y_{1,2}$ are the individual offsets found in the dense zone.

The standard deviations are determined by the equations:

$$s^2(X_{1,2}) = \frac{\sum (x_{1,2} - X_{1,2})^2}{DF_{1,2}} \text{ and} \quad \text{eq. 3a)}$$

$$s^2(Y_{1,2}) = \frac{\sum (y_{1,2} - Y_{1,2})^2}{DF_{1,2}} \quad \text{eq. 3b)}$$

where $DF_{1,2}$ is the degrees of freedom of the average and equal to ($N_{1,2} - 1$).

Similar statements can be made with respect to layer 2 and the electrical failure layer "e". The inspection results on layer "m" are shown to have a known offset to those on layers "p" and "n". Additionally, the offsets between the inspection results on layers "m" and "p" and the locations of the electrical failures on layer "e" are known. (In the case of the electrical bit maps for which row and column failures are used in the dense zone calculations, the number of elements in the dense zones for the x and y offsets may not be the same resulting in slightly different error statistics, as will be appreciated by one of ordinary skill in the art.)

Overlay offsets may not be determined for all layers inspected because the procedure may fail as discussed above, as is shown in the case of layer "3".

In some cases, such as the in-line layers labeled group A in FIG. 12, the overlay offset between layers "1" and "e" can be determined via layer "2". By analogy with equations 1, one can write:

$$x_2 = x_e + \Delta X_{2,e} \text{ with some standard deviation } s(\Delta X_{2,e}) \quad \text{eq. 4a)}$$

and $$y_2 = y_e + \Delta Y_{2,e} \text{ with some standard deviation } s(\Delta Y_{2,e}). \quad \text{eq. 4b)}$$

Combining equations 1 and equations 2 results in $$x_1 = x_e + \Delta X_{1,e} \text{ with some standard deviation } s(\Delta X_{e,1}) \quad \text{eq. 5a)}$$

and $$y_1 = y_e + \Delta Y_{1,e} \text{ with some standard deviation } s(\Delta Y_{e,1}), \quad \text{eq. 5b)}$$

where the offsets are given by the equations:

$$\Delta X_{1,e} = \Delta X_{2,e} + \Delta X_{1,2} \text{ and} \quad \text{eq. 6a)}$$

and $$\Delta Y_{1,e} = \Delta Y_{2,e} + \Delta Y_{1,2} \quad \text{eq. 6b)}$$

The uncertainties in the offsets between layers "e" and "1" will be greater than the uncertainty in either the offset between "2" and "e" or that between "1" and "2". In the case that the offsets between layers are independent of each other, one can write:

$$s(\Delta X_{e,1}) = \sqrt{\frac{DF_{e,2} \times s(\Delta X_{e,2})^2 + DF_{2,1} \times s(\Delta X_{2,1})^2}{(DF_{e,2} + DF_{2,1})}} \text{ and} \quad \text{eq. 7a)}$$

$$s(\Delta Y_{e,1}) = \sqrt{\frac{DF_{e,2} \times s(\Delta Y_{e,2})^2 + DF_{2,1} \times s(\Delta Y_{2,1})^2}{(DF_{e,2} + DF_{2,1})}} \quad \text{eq. 7b)}$$

The number of degrees of freedom of the offset between layers e and 2 is the sum of those between layers e and 1 and layers 1 and 2.

Those of ordinary skill in the statistical arts will know of other algorithms for calculation of the uncertainty of the estimate of the offset of the coordinate systems between layers e and 1 based on the estimates of the offset between layers e and 2 and the offset between layers 2 and 1.

It can be proven by induction that eqs. 6 can be extended to in the case of k steps between two layers to:

$$\vec{X} = \sum_{i=1}^{k} \vec{X}_i \quad \text{eq. 8))}$$

where the sum is a vector sum over the vector offsets.

Similarly, eqs. 7 can be extended by induction for the case of k steps between two layers to:

$$s(\Delta \vec{X}_{1,k}) = \sqrt{\frac{\sum_{i=1}^{k} DF_{i,i+1} \times s(\Delta \vec{X}_{1,k})^2}{\sum_{i=1}^{k} DF_{i,i+1}}} \quad \text{eq. 9)}$$

where the number of degrees of freedom of the whole is the sum of the degrees of freedom of the k steps along, the path.

In other cases there may be more correlation equations than there are variables so that the offsets are overdetermined. This occurs with respect to the in-line inspection layers labeled B in FIG. 12 and the electrical failure level "e".

Following the previous discussion, layer n can be related to layer e with either of the following set of equations:

$$\Delta X_{n,e} = \Delta X_{m,e} + \Delta X_{m,n}$$

$$\Delta Y_{n,e} = \Delta Y_{m,e} + \Delta Y_{m,n} \quad \text{eqs. 10)}$$

or $$\Delta X_{n,e} = \Delta X_{p,e} + \Delta X_{p,n}$$

$$\Delta Y_{n,e} = \Delta Y_{p,e} + \Delta Y_{p,n} \quad \text{eqs. 11)}$$

Eqs. 7a and 7b suggest an answer as to which of the above sets of equations should be used. The standard deviation of each independent path is calculated. The path with the smaller uncertainty, e.g. the standard deviation or standard error, is chosen as the best estimate of the offset of the coordinate system of the inspection data for the layer n from the coordinate system of the electrical failure map, layer e.

In some cases, advantage can be taken of the extra information available on the correlations within group B and between members of group B and layer "e" to improve the estimates of the offsets.

Figure 13:
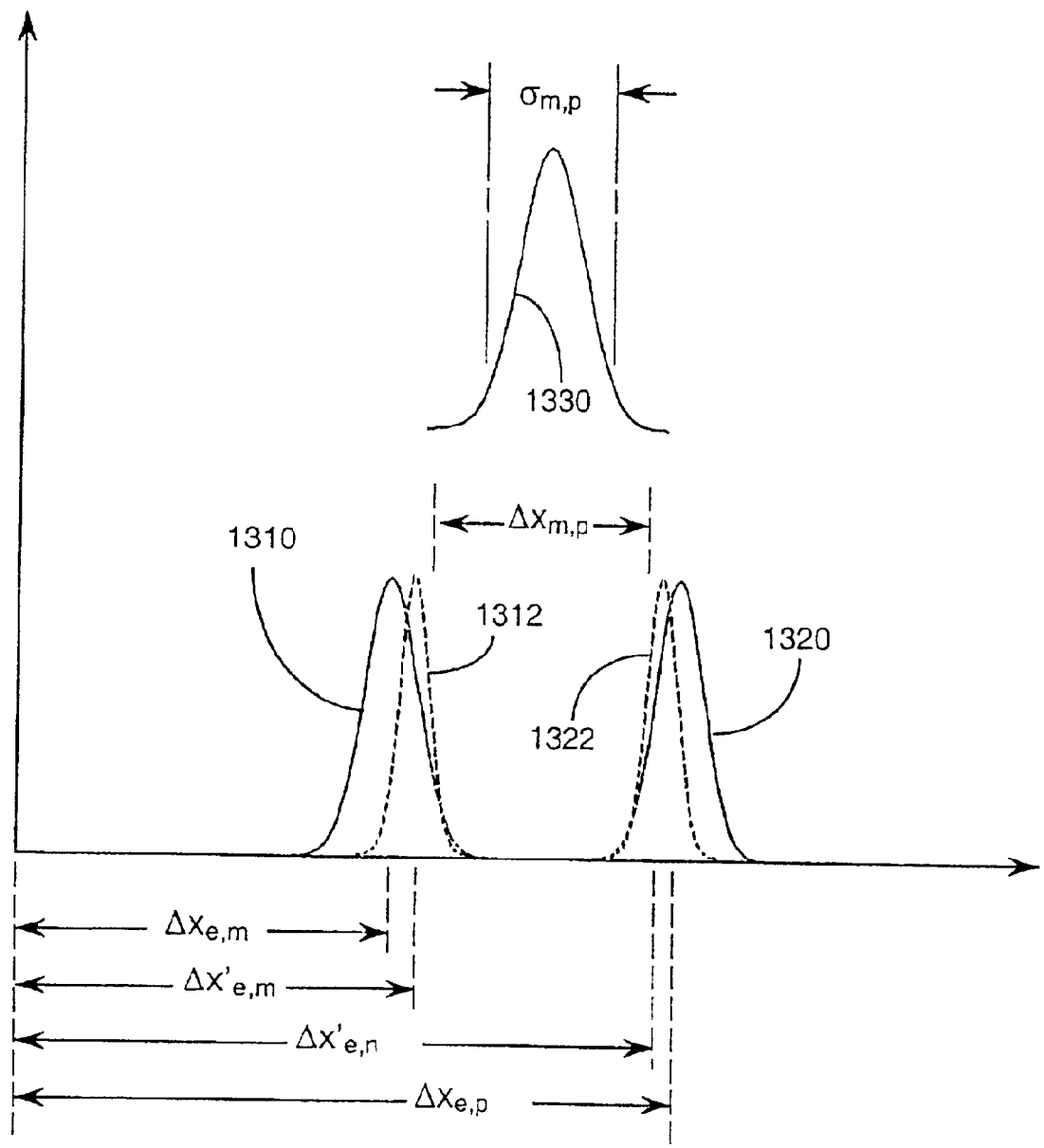
FIG. 13 is graphical illustration of the measured distribution of x coordinate offsets between various layers.

This advantage is illustrated in FIG. 13. The curve 1310 represents the measured distribution of x coordinate offsets between layers "e" and "m" while the curve 1320 represents the measured distribution of x coordinate offsets between layers "e" and "p". From these distributions the offsets $\Delta X_{e,m}$ and $\Delta X_{e,p}$ are found. However, the distribution of the x offsets between layers "m" and "p" is also measured. In the illustration, it is assumed that the expected value of $\Delta X_{m,p}$ is less than the value of $[\Delta X_{e,p} - \Delta X_{e,m}]$. This is not really contradictory because the difference is within the uncertainties in the determination of the three values. In fact, the information from the offset between layers m and p can be used to refine the estimates of the values of the offsets $\Delta X_{e,m}$ and $\Delta X_{e,p}$. The improved estimates are shown by the dashed lines 1312 and 1322 in FIG. 13.

Formally, assume that there two independent paths are found to estimate the offsets between layers f and g. Let us denote one path by $\vec{U}$ and the other path by $\vec{V}$. Then $$\Delta X_{U\_f,g} = \sum_{l=1}^{n_u} \Delta X_{Ul} \text{ and} \qquad \text{eqs. 12)}$$

$$\Delta X_{V\_f,g} = \sum_{l=1}^{n_v} \Delta X_{Vl}$$

where the path $\vec{U}$ has $n_U$ steps and the path $\vec{V}$ has $n_V$ steps.

The offset $\Delta X_{U\_f,g}$ has $DF_U$ degrees of freedom and the path $\Delta X_{V\_f,g}$ has $DF_V$ degrees of freedom that are given by the equations:

$$DF_U = \sum_{l=1}^{n_u} DF_l \text{ and} \qquad \text{eqs. 13)}$$

$$DF_V = \sum_{l=1}^{n_v} DF_l$$

The standard deviations associated with these components are:

$$s(\Delta X_U) = \sqrt{\frac{\sum_{l=1}^{n_u} [DF_{lU} \times s(\Delta X_U)^2]}{\sum_{l=1}^{n_u} DF_{lU}}} \text{ and} \qquad \text{eqs. 14)}$$

$$s(\Delta X_V) = \sqrt{\frac{\sum_{l=1}^{n_v} [DF_{lV} \times s(\Delta X_V)^2]}{\sum_{l=1}^{n_v} DF_{lV}}}$$

The best estimate of the offset between f and g is given by:

$$\Delta \overline{X}_{f,g} = \frac{(DF_U + n_U) \times \Delta X_{U\_f,g} + (DF_V + n_V) \times \Delta X_{V\_f,g}}{(DF_U + n_U) + (DF_V + n_V)} \qquad \text{eq. 15)}$$

The standard deviation of this estimate is given by:

$$s(\Delta \overline{X}_{f,g}) = \sqrt{\frac{DF_U \times s(\Delta X_{U\_f,g})^2 + DF_V \times s(\Delta X_{V\_f,g})^2}{(DF_U + DF_V)}} \qquad \text{eq. 16)}$$

Figure 14:
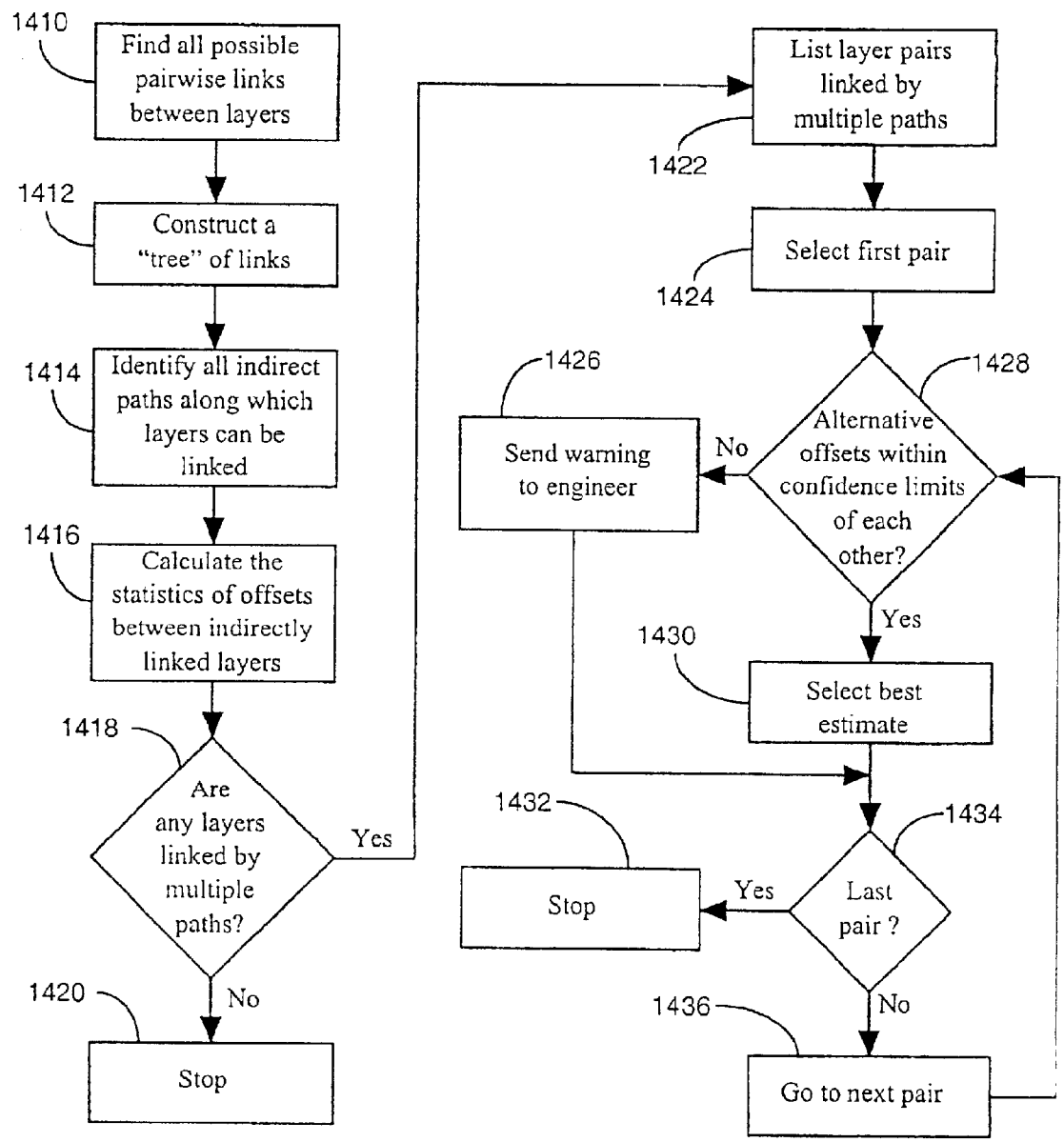
FIG. 14 is a flow diagram illustrating the implementation of one method of the present invention.

An embodiment for finding the offsets between the coordinate systems of at least three sets of data representing the defects found in the inspections on three layers of an integrated circuit wafer is summarized schematically in the flow chart shown in FIG. 14.

The method begins by finding all of the offsets that can be determined between pairs of layers by any of several alternative methods described in this disclosure as is shown in act 1410. For convenience, the offsets found between the coordinates on the various layers will be referred to as the links between the layers. Once the possible links between the pairs of layers are known, a tree of links similar to that illustrated in FIG. 11 is constructed as indicated in act 1412 of FIG. 14.

As has been discussed, if the links between layers a and b and between layers b and c are known, the link between layers a and c can be found. The link between two layers that is found as a result of links that these two have to other layers is referred to as an indirect link. Once the tree of direct links is established as indicated in act 1412, the possible indirect paths can be found by several methods including an exhaustive search, as is indicated in act 1414. Once the indirect links are identified, the statistics can be calculated using eqs. 6 through 9 as is indicated in act 1416.

As indicated in query 1418, the resulting links are now tested to ascertain if any layers are linked by multiple paths, i.e. by paths which provide links through different sets of layers. If not, the process terminates. If there are layers linked with multiple paths, the layers with these multiple paths are listed, as is shown in act 1422.

A first pair with multiple paths is selected at act 1424 and tested to see if the coordinate offsets indicated by the alternative paths agree within some confidence limit at query 1428. If not, a warning is sent to the operator or engineer at act 1426. If there is agreement, a best estimate is selected at act 1430 by either of the alternative methods discussed previously. This process is repeated until all of the pairs linked by multiple paths are examined, query 1434 and acts 1432 and 1436.

Although the teachings of this invention have been described in terms of inspection in the manufacture of integrated circuits, it should be apparent to one of ordinary skill in the art that the teachings of this invention can be applied to other manufacturing operations in which inspections are performed on various layers during the manufacturing process and it is desired to remove offsets between the inspection data from various layers. Non-limiting examples of this might be in the manufacture of display panels or multilevel printed wiring boards.

While embodiments and applications of this invention have been shown and described, it would be apparent to those skilled in the art that many more modifications than mentioned above are possible without departing from the inventive concepts herein. For example, although the present invention has been described in detail regarding the utilization of specific mathematical equations, it should be understood by one skilled in the art that there are a plurality of equations that may be utilized instead of those described herein. The invention, therefore, is not to be restricted except in the spirit of the appended claims.

What is claimed is:

1. A method for determining the offset between at least two origins of a coordinate system used for at least two different defect inspection spaces, the method comprising:

collecting multiple sets of data spanning said defect inspection spaces;

filtering said data sets to remove points that introduce noise into correlation calculations;

determining whether different said data sets show correlation;

selecting pairs of said data sets showing correlation greater than or equal to a metric, if different said data sets show correlation; and calculating coordinate offsets of said origins based on the said selected pairs of said data sets.

2. An apparatus for determining the offset between at least two origins of a coordinate system used for at least two different defect inspection spaces, comprising:

means for collecting multiple sets of data spanning said defect inspection spaces;

means for filtering said data sets to remove points that introduce noise into correlation calculations;

means for determining whether different said data sets show correlation;

means for selecting pairs of said data sets showing correlation greater than or equal to a metric, if different said data sets show correlation; and means for calculating coordinate offsets of said origins based on the said selected pairs of said data sets.

3. A program storage device readable by a machine, tangibly embodying a program of instructions executable by the machine to perform a method of determining the offset between at least two origins of a coordinate system used for at least two different defect inspection spaces, the method comprising:

collecting multiple sets of data spanning said defect inspection spaces;

filtering said data sets to remove points that introduce noise into correlation calculations;

determining whether different said data sets show correlation;

selecting pairs of said data sets showing correlation greater than or equal to a metric, if different said data sets show correlation; and calculating coordinate offsets of said origins based on the said selected pairs of said data sets.

4. A method for determining the offset between at least two origins of a coordinate system used for at least two different defect inspections of a wafer at, at least, a first layer and a second layer and with integrated circuits disposed on it, the method comprising:

filtering defect data;

identifying each defect in said second layer lying near each defect in said first layer;

computing coordinate differences between defects in said first layer and said defects in said second layer;

finding dense zones where there are a relatively high density of offsets;

determining whether offsets in said dense zones are distributed randomly;

calculating descriptive statistics, including at least average offsets and confidence limits, for said dense zones if said offsets are not distributed randomly; and reporting average offset and confidence limits.

5. The method of claim 4, wherein said finding of dense zones comprises:

dividing the range of each coordinate offset into a number of equal intervals; and selecting the interval with the greatest count of offsets as the dense zone.

6. An apparatus for determining the offset between at least two origins of a coordinate system used for at least two different defect inspections of a wafer at, at least, a first layer and a second layer and with integrated circuits disposed on it, comprising:

means for filtering defect data;

means for identifying each defect in said second layer lying near each defect in said first layer;

means for computing coordinate differences between defects in said first layer and said defects in said second layer;

means for finding dense zones where there are a relatively high density of offsets;

means for determining whether offsets in said dense zones are distributed randomly;

means for calculating descriptive statistics, including at least average offsets and confidence limits, for said dense zones if said offsets are not distributed randomly; and means for reporting average offset and confidence limits.

7. The apparatus of claim 6, wherein said means for finding of dense zones comprises:

means for dividing the range of each coordinate offset into a number of equal intervals; and means for selecting the interval with the greatest count of offsets as the dense zone.

8. A program storage device readable by a machine, tangibly embodying a program of instructions executable by the machine to perform a method for determining the offset between at least two origins of a coordinate system used for at least two different defect inspections of a wafer at, at least, a first layer and a second layer and with integrated circuits disposed on it, the method comprising:

filtering defect data;

identifying each defect in said second layer lying near each defect in said first layer;

computing coordinate differences between defects in said first layer and said defects in said second layer;

finding dense zones where there are a relatively high density of offsets;

determining whether offsets in said dense zones are distributed randomly;

calculating descriptive statistics, including at least average offsets and confidence limits, for said dense zones if said offsets are not distributed randomly; and reporting average offset and confidence limits.

9. The program storage device of claim 8, wherein said finding of dense zones further comprises:

dividing the range of each coordinate offset into a number of equal intervals; and selecting the interval with the greatest count of offsets as the dense zone.

10. A method for determining the offset between at least three origins of a coordinate system used for at least three different defect inspections of a wafer with integrated circuits disposed on it, the method comprising:

finding all possible pairwise links between layers;

constructing a tree of links;

identifying from said tree all indirect paths along which layers can be linked;

calculating statistics of offsets between indirectly linked layers;

determining whether any pair of layers are linked by multiple paths;

listing each pair of layers linked by multiple paths, if there are any pair of layers linked by multiple paths;

selecting a listed pair of layers that have not been previously selected;

determining whether offsets associated with said listed pair of layers are within confidence limits of each other;

selecting the best estimate of said offsets;

determining whether the system has selected all the of the listed pairs; and selecting a listed pair of layers that have not been previously selected.

11. The method of claim 10, wherein selecting said best estimate comprises averaging said offsets associated with said listed layer pairs.

12. The method of claim 10, wherein selecting said best estimate comprises calculating the median of said offsets associated with said listed layer pairs.

13. An apparatus for determining the offset between at least three origins of a coordinate system used for at least three different defect inspections of a wafer with integrated circuits disposed on it, comprising:

means for finding all possible pairwise links between layers;

means for constructing a tree of links;

means for identifying from said tree all indirect paths along which layers can be linked;

means for calculating statistics of offsets between indirectly linked layers;

means for determining whether any pair of layers are linked by multiple paths;

means for listing each pair of layers linked by multiple paths, if there are any pair of layers linked by multiple paths;

means for selecting a listed pair of layers that have not been previously selected;

means for determining whether offsets associated with said listed pair of layers are within confidence limits of each other;

means for selecting the best estimate of said offsets;

means for determining whether the system has selected all the of the listed pairs; and means for selecting a listed pair of layers that have not been previously selected.

14. The apparatus claim 13, wherein said means for selecting best estimate further comprises means for averaging said offsets associated with said listed layer pairs.

15. The apparatus of claim 13, wherein said means for selecting said best estimate comprises means for calculating the median of said offsets associated with said listed layer pairs.

16. A program storage device readable by a machine, tangibly embodying a program of instructions executable by the machine to perform a method for determining the offset between at least three origins of a coordinate system used for at least three different defect inspections of a wafer with integrated circuits disposed on it, the method comprising:

finding all possible pairwise links between layers;

constructing a tree of links;

identifying from said tree all indirect paths along which layers can be linked;

calculating statistics of offsets between indirectly linked layers;

determining whether any pair of layers are linked by multiple paths;

listing each pair of layers linked by multiple paths, if there are any pair of layers linked by multiple paths;

selecting a listed pair of layers that have not been previously selected;

determining whether offsets associated with said listed pair of layers are within confidence limits of each other;

selecting the best estimate of said offsets;

determining whether the system has selected all the of the listed pairs; and selecting a listed pair of layers that have not been previously selected.

17. The program storage device of claim 16, wherein said selecting the best estimate comprises averaging said offsets associated with said listed layer pairs.

18. The program storage device of claim 16, wherein said selecting the best estimate comprises calculating the median of said offsets associated with said listed layer pairs.

* * * * *